(12) United States Patent
Maquieira (10) Patent No.: US 10,702,155 B2
(45) Date of Patent: Jul. 7, 2020

(54) TRANSMISSION HANDLING OF MEDICAL DEVICES

(71) Applicant: LINDACARE NV, Leuven (BE)

(72) Inventor: Miguel Maquieira, Pontevedra (ES)

(73) Assignee: LINDACARE NV, Leuven (BE)

( * ) Notice: Subject to any disclaimer, the term of this patent is extended or adjusted under 35 U.S.C. 154(b) by 0 days.

(21) Appl. No.: 16/315,793

(22) PCT Filed: Apr. 27, 2017

(86) PCT No.: PCT/EP2017/060032
§ 371 (c)(1),
(2) Date: Jan. 7, 2019

(87) PCT Pub. No.: WO2018/007037
PCT Pub. Date: Jan. 11, 2018

(65) Prior Publication Data
US 2019/0150740 A1    May 23, 2019

(30) Foreign Application Priority Data

Jul. 7, 2016    (EP) .................................... 16178399

(51) Int. Cl.
*G08B 1/08*      (2006.01)
*A61B 5/00*      (2006.01)
(Continued)

(52) U.S. Cl.
CPC .......... *A61B 5/0031* (2013.01); *A61B 5/0022* (2013.01); *A61B 5/686* (2013.01);
(Continued)

(58) Field of Classification Search
CPC ..... A61B 5/0031; A61B 5/0022; A61B 5/686; A61B 5/0006; A61B 5/747; A61B 5/6801;
(Continued)

(56) References Cited

U.S. PATENT DOCUMENTS 8,827,904 B2 * 9/2014 Ball ..................... A61B 5/0031
600/300
2004/0122297 A1   6/2004 Stahmann et al.
(Continued)

OTHER PUBLICATIONS

Extended European Search Report from EP Application No. 16178399. 8, dated Jan. 23, 2017.
(Continued)

*Primary Examiner* — Anh V La
(74) *Attorney, Agent, or Firm* — Workman Nydegger (57) ABSTRACT

A method for handling an Implantable Medical Device, IMD, transmission from an IMD provider such that the transmission comprises one or more alerts and/or IMB data attributes indicative for a status of the IMD or the patient. The alert comprises a provider specific alert priority. The method comprises the following steps: retrieving the IMD transmission from the IMD provider; and assigning to the one or more alerts a generic alert severity based on a predetermined mapping between the provider specific alert priority and the generic alert severity; and/or calculating an IMD data severity based on the IMD data attributes; and calculating a transmission severity based on the generic alert severity assigned to the one or more alerts and/or the IMD data severity.

11 Claims, 5 Drawing Sheets

(51) Int. Cl.
  *A61N 1/372*  (2006.01)
  *G08B 23/00* (2006.01)
  *A61N 1/365*  (2006.01)
  *G06F 16/95*  (2019.01)

(52) U.S. Cl.
  CPC ......... *A61N 1/37282* (2013.01); *G08B 23/00* (2013.01); *A61B 5/0006* (2013.01); *A61B 5/747* (2013.01); *A61N 1/365* (2013.01); *G06F 16/95* (2019.01)

(58) Field of Classification Search
  CPC ........... A61B 5/486; A61B 5/742; A61B 5/72; A61B 5/0004; A61B 5/7475; A61B 5/7435; A61B 5/6898; G08B 23/00; A61N 1/37282; A61N 1/365; G06F 16/95; G16H 10/40; G16H 40/40; G16H 40/63
  USPC ................. 340/539.12, 539.1, 573.1, 870.1; 600/347, 345, 365, 309
  See application file for complete search history.

(56) References Cited

U.S. PATENT DOCUMENTS

| | | | |
|---|---|---|---|
| 2006/0017575 A1 | 1/2006 | McAdams | |
| 2007/0279211 A1 | 12/2007 | Fenske et al. | |
| 2008/0157980 A1* | 7/2008 | Sachanandani | A61B 5/0031 340/573.1 |
| 2008/0278332 A1* | 11/2008 | Fennell | A61B 5/0002 340/573.1 |
| 2010/0123587 A1 | 5/2010 | Walls | |
| 2011/0208268 A1 | 8/2011 | Brown | |
| 2011/0260855 A1* | 10/2011 | John | A61B 5/0031 340/539.12 |
| 2012/0108917 A1 | 5/2012 | Libbus et al. | |

OTHER PUBLICATIONS

International Search Report and Written Opinion from PCT Application No. PCT/EP2017/060032, dated Jul. 19, 2017.

\* cited by examiner

TRANSMISSION HANDLING OF MEDICAL DEVICES

FIELD OF THE INVENTION

The present invention relates to the field of implantable medical devices or shortly IMDs such as for example pacemakers. More particular, the invention relates to the handling of transmissions that are generated by the IMDs and made available by an IMD provider.

BACKGROUND OF THE INVENTION

Most IMDs available on the market today can communicate wirelessly with an external communication device. An IMD will monitor both the condition of the patient and the condition of the IMD itself. When an abnormal condition is detected, the IMD issues an alert and communicates it as part of a transmission to the external communication device. Transmissions may also be sent if there is no abnormal condition. In such a case the transmission may comprise some data attributes indicative for the status of the device or the status of the patient. Transmissions may further be initiated by the IMD itself or by the patient. Typically, to save power, the external communication device is located within close range of the patient in order to limit the power consumption of the wireless communication. The external communication device functions as router and forwards the alert to a central IMD management system.

Typically, such an IMD management system is managed by the vendor or provider of the IMD. Medical or technical staff can then log onto this system to view and handle transmissions generated by the IMDs.

US2010/0123587 discloses such an alert management system that can be used by a provider of IMDs. Incoming alerts are managed by processing values of parameters related to the alert such that appropriate actions can be taken. This way a relatively small number of parameters can be defined to manage a relatively large number of different alerts.

US2006/0017575 discloses such an alert management system that can be accessed by a care giver through a web interface. The care giver may then change different settings for the alerts and even define certain clinical or device alerts.

US2012/0108917 discloses such an alert management system wherein the IMD-generated alerts can be customized in many ways so as to suit the health condition and personal circumstances of each individual patient. The alerts can also be customized to provide an appropriate alert for each individual patient corresponding to a patient-initiated emergency notification transmission from the patient's adherent device.

A problem with the existing solutions is that all IMD management systems are vendor or provider specific. Medical or technical staff has to access all IMD management systems separately for each vendor or provider and thus lacks a unified overview.

SUMMARY OF THE INVENTION

It is an object of the present invention to overcome the above problem and to provide an IMD alert management system that can handle different types of IMD transmission and that can prioritize the handling of the patients according to these different transmissions.

This object is achieved, according to a first aspect, by a computer-implemented method for handling an Implantable Medical Device, IMD, transmission from an IMD provider. The IMD transmission is related to a patient and comprises one or more alerts and/or IMD data attributes indicative for a status of the IMD or the patient. An alert comprises a provider specific alert priority. The method further comprises the following steps:
  retrieving the IMD transmission from the IMD provider; and
  assigning to the one or more alerts a generic alert severity based on a predetermined mapping between the provider specific alert priority and the generic alert severity; and/or calculating an IMD data severity based on the IMD data attributes; and
  calculating a transmission severity based on the generic alert severity assigned to the one or more alerts and/or based on the IMD data severity.

A transmission severity is thus calculated for a received transmission, i.e., an indication of the severity of the specific transmission. The severity is further based on the alerts in the transmission, on the IMD data attributes or both. The transmission severity is thus an IMD independent measure of how urgently a transmission should be handled, for example by medical or technical staff. The method further makes use of a mapping between the provider specific alerts and the generic alert severity. In other words, any alert from any supported provider can be converted to the same measure that indicates the urgency of the alert.

It is an advantage that transmissions from any IMD provider is assigned with a single measure for any type of transmission and regardless of the amount of IMD data or alerts in the transmission. This way, transmissions can be prioritized independently from the IMD provider.

Optionally the method further comprises:
  overriding the generic alert severity of each of the one or more alerts by an alert specific override factor associated with a type of the respective alert or the patient.

In a conventional alert management system, the alerts have a priority such that medical staff may prioritize the handling of the alerts. However, it may be desirable to make a distinction in priority between alerts with the same priority. This is accomplished by the overriding factor which will change the alert severity according on the alert itself and the patient's IMD for which the alert is triggered.

Advantageously calculating the transmission severity further comprises calculating a weighted sum between the IMD data severity and the generic alert severity of the one or more alerts of the IMD transmission. This way, the contribution of the alerts and IMD data to the transmission severity may be chosen.

According to an embodiment, method further comprises:
  calculating a patient follow-up priority based on the transmission severity.

In other words, the severity of the transmission contributes to the priority of the patient that needs to be handled first. This way, a priority list of patients may be obtained independently of the IMD provider.

Advantageously, the calculating the patient follow-up priority is further based on a patient specific weight factor. This way medical staff may give higher priority to some specific patients, but the priority still depends on the transmissions. Therefore, when there is a transmission from a patient with a high patient specific weight factor, but the transmission itself has a low severity, the patient will be put higher on the patient follow-up priority list.

More advantageously, the calculating the patient follow-up priority is further based on one or more weighted earlier transmission severities obtained from earlier IMD transmissions. This way, the history of a patient is taken into account for moving him upwards or downwards on the patient follow-up priority list. Again, by doing this by weighting the earlier transmission severities this can be done in an easy and efficient manner.

When a patient follow-up priority is calculated or updated, the method may further comprise:
classifying the patient into a priority group according to the calculated patient follow-up priority.
This priority groups may for example be selected from the group of:
a first level indicative for a low medical priority, and
a second level indicative for a medium medical priority, and
a third level indicative for a high medical priority.

This way, instead of having a cluster of alerts and IMD data each with their specific priority or values, an IMD independent classification is obtained which is focussed on the patients but takes into account the complete set of alerts and IMD data.

According to a second aspect, the invention relates to a computer program product comprising computer-executable instructions for performing the method according to the first aspect when the program is run on a computer.

According to a third aspect, the invention relates to a computer readable storage medium comprising the computer program product according to claim the second aspect.

According to a fourth aspect, the invention relates to a data processing system programmed for carrying out the method according to the first aspect.

DETAILED DESCRIPTION OF EMBODIMENT(S)

Figure 1:
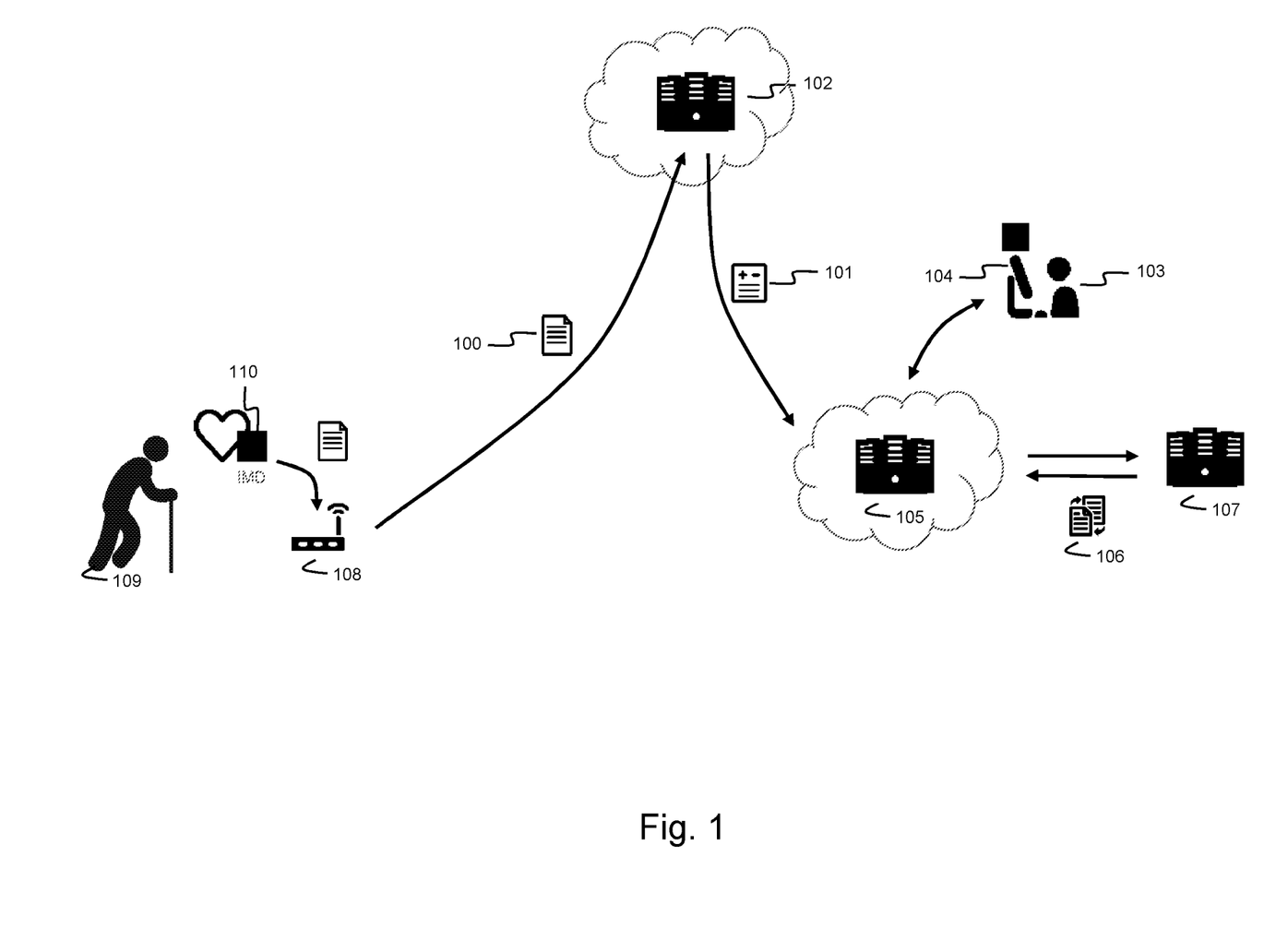
FIG. 1 illustrates an IMD management system according to an embodiment of the invention implemented on top of a vendor specific IMD management system.

FIG. 1 illustrates the handling of IMD related transmissions 100. An implantable medical device or IMD 110 is implanted in a patient 109. The IMD 110 comprises a transmission means for communicating data related to the patient or the IMD to a central IMD management system 102. The IMD 110 may also trigger alerts when a condition is not met and transmit these alerts to the system 102. Alerts and/or IMD data are typically bundled in a single piece of data 100, further referred to as an IMD transmission or just transmission. As IMD devices are typically battery powered, energy efficiency is very important. To this end, the IMD device 110 may further communicate the transmissions 100 to a nearby routing device 108 according to a low-energy wireless protocol. The routing device 108 then transmits the transmissions 100 further to the central IMD management system 102.

IMD management system 102 is typically vendor specific, i.e., it only handles transmissions from a specific subset of IMD's that are for example produced or sold by the vendor. Such an IMD management system 102 may offer a user interface such that a user such as medical or technical staff can logon onto the system 102 and handle the alerts generated by the IMD's.

According to an embodiment, a system 105 is provided that retrieves the IMD transmissions 100 from each of the IMD vendor specific management systems 102. The system 105 further processes the transmissions and derives therefrom a patient follow-up priority list. In order to do so, system 105 may retrieve other useful data 106 from other management systems 107. Data 106 may for example comprise patient specific data retrieved form a patient management system managing patient data for a hospital. System 105 offers a user interface that may be displayed remotely on a client device 104. A user 103 of the client device such as medical or technical staff of a hospital may then consult the patient follow-up priority list. System 105 may be located in a hospital or data centre. System 105 may also delocalized, i.e., steps performed by system 105 may be run in the cloud as a virtual system.

Figure 2:
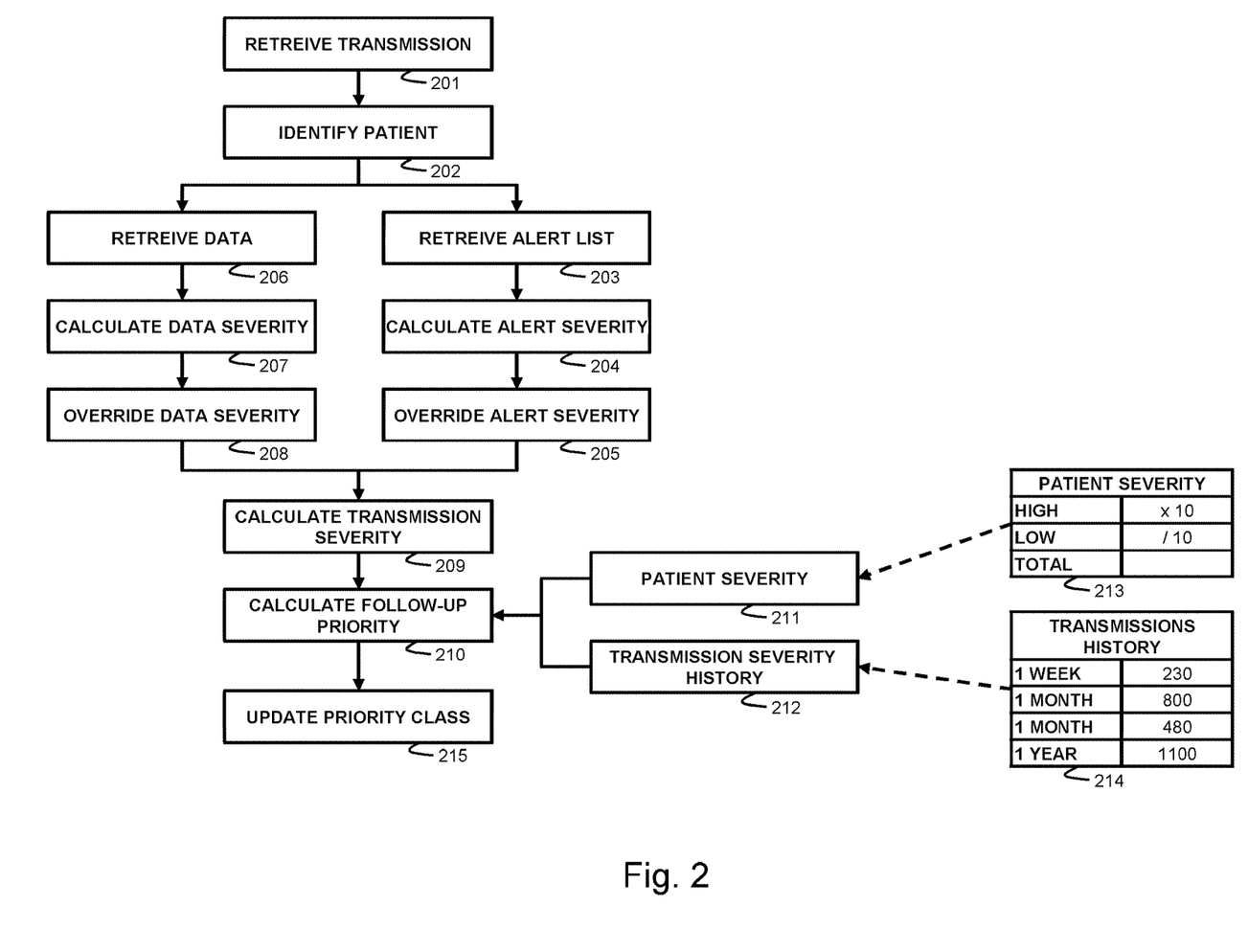
FIG. 2 illustrates steps executed by a computing system for handling transmissions from different IMD providers according to an embodiment of the invention.
Figure 3:
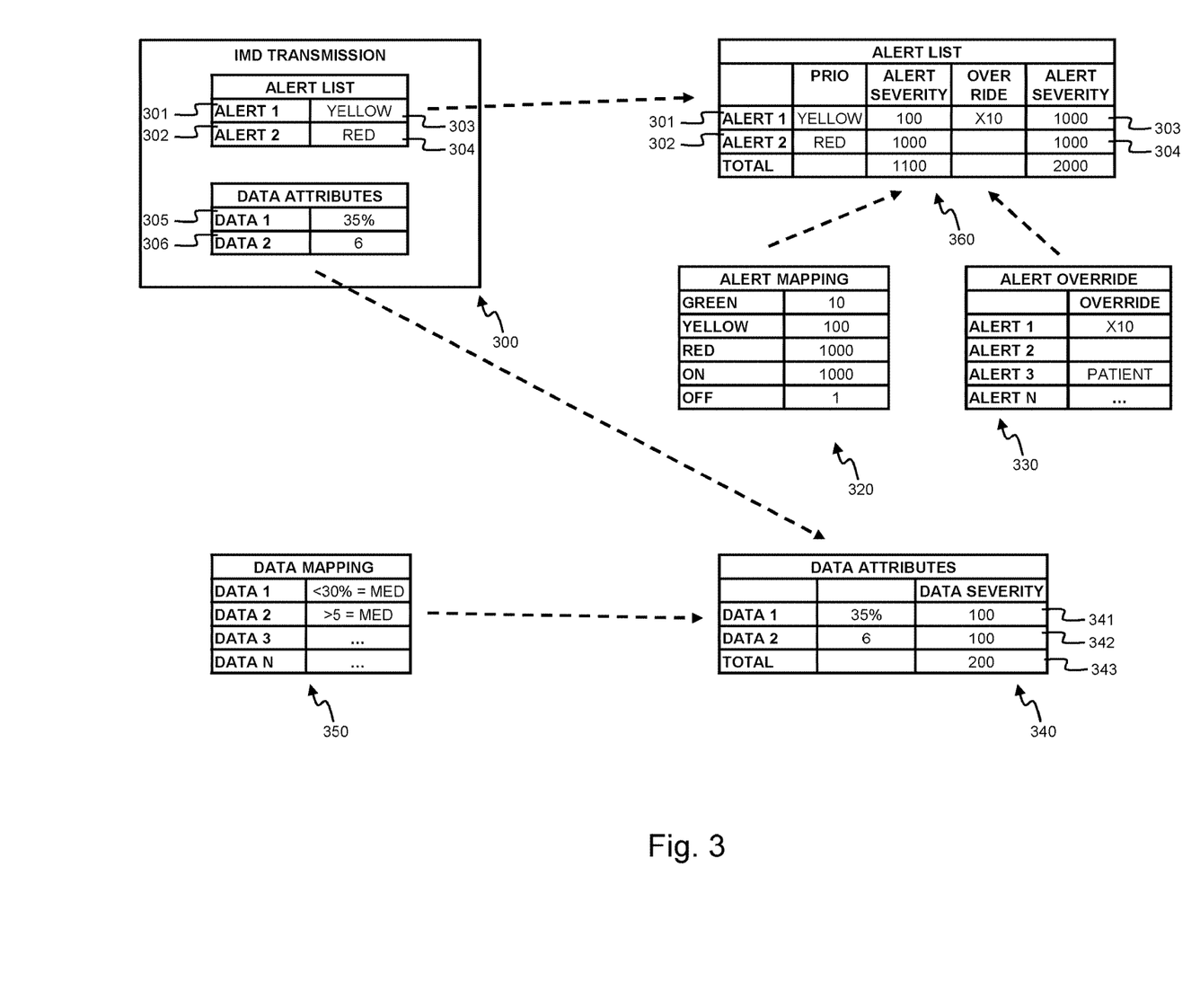
FIG. 3 illustrates a retrieved IMD transmission and related mapping tables for deriving a patient follow-up priority according to an embodiment of the invention.

FIG. 2 illustrates steps performed by the system 105 in order to produce a follow-up priority list of patients. The different steps will further be illustrated by references to FIG. 3 illustrating an example of an IMD transmission 300 and related mapping tables 320, 330, 350, 340.

In a first step 201, system 105 retrieves a transmission from IMD provider 102, for example transmission 300. System 105 may retrieve a set 101 of transmissions at once from the provider 102, i.e., in batch. The retrieval may further be performed at predetermined moments in time, i.e., by a pull mechanism. Alternatively, the retrieval may be performed by a push mechanism, i.e., the IMD provider sends to the transmissions 101 to the system 105, for example when they become available.

IMD transmission 300 comprises alerts 301 and 302 each related to respective alert priority 303 and 304. These alert priorities are vendor specific and may even be named differently between IMD vendors. Alerts 301, 302 may further be described by a code or text string.

IMD transmission 300 further comprises IMD data attributes 305 and 306. An IMD data attribute provides further information about the patient or the IMD itself. Examples of IMD data attributes are:
Battery level;
Electrical resistance;
Sensor measurements;
Patient average hearth rate;
The ventricular chambers paced during re-synchronization pacing.
The mean atrial heart rate over the specified time period.
IMD attributes may further be specified according to the IDCO profile, i.e., the Implantable Device Cardiac Observation profile, specifying a mechanism for transmission, and processing of discrete data elements and report attachments associated with cardiac device observations.

In a second step 202, the system 105 identifies the patient 109. In order to identify the patient, the system 105 may retrieve further data from a patient management system. The patient 109 may for example be identified by relating a device identification attribute in the IMD data to the patient. Alternatively, the IMD provider 102 may already have identified the patient and provide the identification to the system 105 along with the transmissions 101.

In the following steps 203 to 205, the alert priorities in the transmission are converted to an alert severity, i.e., a single measure is calculated from an alert. This way, the priorities of different alerts from different IMD vendors become comparable with each other. In the first step 203 system 105 retrieves the alert list from the IMD transmission for example by making a copy 360. Then, in step 204, system 105 calculates the alert severity. The system 105 first consults mapping table 320. This table comprises a relation between all possible alert priorities and the generic alert severity. Based on the mapping table 320, the alert priorities 301, 302 are converted to an alert severity. For example, alert 301 with priority level 'YELLOW' gets an alert severity '100' and alert 302 with priority level 'RED' gets alert severity '1000'. Then, optionally, the alert severity may be overridden by alert overriding factor in step 205. These overriding factors are specified in table 330. The alert overriding factor may be specific for a certain alert. For example, for all alerts of the type 'ALERT 1', the severity is multiplied by 10 ('×10'). The alert overriding factor may further be patient specific. For example, for all alerts of the type 'ALERT 3', the severity is increased or decreased by a factor related to the patient. This factor may then be retrieved from a patient specific table listing all overriding factors assigned to this patient. Then, the alert severities are updated by taking into account the overriding factor thereby obtaining alert severities 303 and 304.

In parallel or sequentially to steps 203 to 205, the system 105 performs steps 206 to 208 in a similar way, i.e., the IMD data attributes 305, 306 in the transmission are converted to an IMD data severity which is a single measure of the priority of all the IMD data together independently from the IMD vendor. In the first step 206 system 105 retrieves all or a subset of the data attributes from the IMD transmission for example by making a copy 340. Then, in step 207, system 105 calculates the IMD severity 340. The system 105 first consults mapping table 350. This table comprises for every data attribute a mapping between the value of the attribute and a level of severity. From this mapping, the severity 341, 342 of each IMD data attribute 305, 306 is calculated. Optionally, similar to step 205, all IMD data severities 341, 342 may be further overridden by a patient specific overriding factor in step 208. Finally all severities are summed to obtain the IMD data severity 343.

In step 209 the system then calculates the transmission severity from the alert severities and IMD data severity. This transmission severity is a measure represented by a single number that relates the severity of the transmission 300 to the other transmissions independently from an IMD vendor. The calculation is performed by a weighted sum between the alert severities and data severity. By choosing the weights appropriately more or less emphasis may be given to either the IMD data or alerts.

In the next step 201, system 105 calculates from the transmission severity, the follow-up priority of the patient, i.e., a single measure indicative for the priority of the patient relative to other patients. According to a first example, the follow-up priority is only based on the transmission severity. The follow-up priority may then be the same as the transmission severity. According to a second example, the follow-up priority is further based on the patient severity 211. The transmission severity is then for example multiplied with a certain factor. These factors may be stored in a patient severity mapping table 213 listing these factors for each severity. In the example of FIG. 2, a patient that is assigned a 'HIGH' patient severity will have its follow-up priority multiplied by ten, a patient that is assigned a 'LOW' patient severity will have its follow-up priority divided by ten. According to a third example, the follow-up priority is further based on the transmission history 212 of the patient, i.e., the earlier calculated transmission severities are also taken into account. These transmission severities may be stored in a table 214.

In a last step 215, the patient may then be assigned to a priority class, for example a 'LOW', 'MEDIUM' or 'HIGH' priority class.

Steps 201 to 215 can be repeated for every received transmission. This way, the follow-up priority of every patient is always up-to-date such that medical or technical staff can always consult which patient needs to be handled first.

According to an embodiment, the follow-up priority is calculated according to the following formula:

$$PFL = (TS_0 \times PS) + \Sigma \log TS_i$$

wherein

PFL is the patient follow up priority as calculated in step 210;

$TS_0$ is the transmission severity as calculated in step 209;

PS is the patient severity as retrieved from table 213;

$TS_i$ are the previously calculated transmission severities as retrieved from table 214.

The transmission severity $TS_0$ is calculated as follows:

$$TS_0 = AS_0 + iwr \cdot IS_0$$

wherein $AS_0$ is the alert severity as calculated in steps 203 to 205;

$IS_0$ is the IMD data severity as calculated in steps 206 to 208;

iwr is a weight factor to determine the contribution of the IMD data severity with respect to the alert severity.

Figure 4:
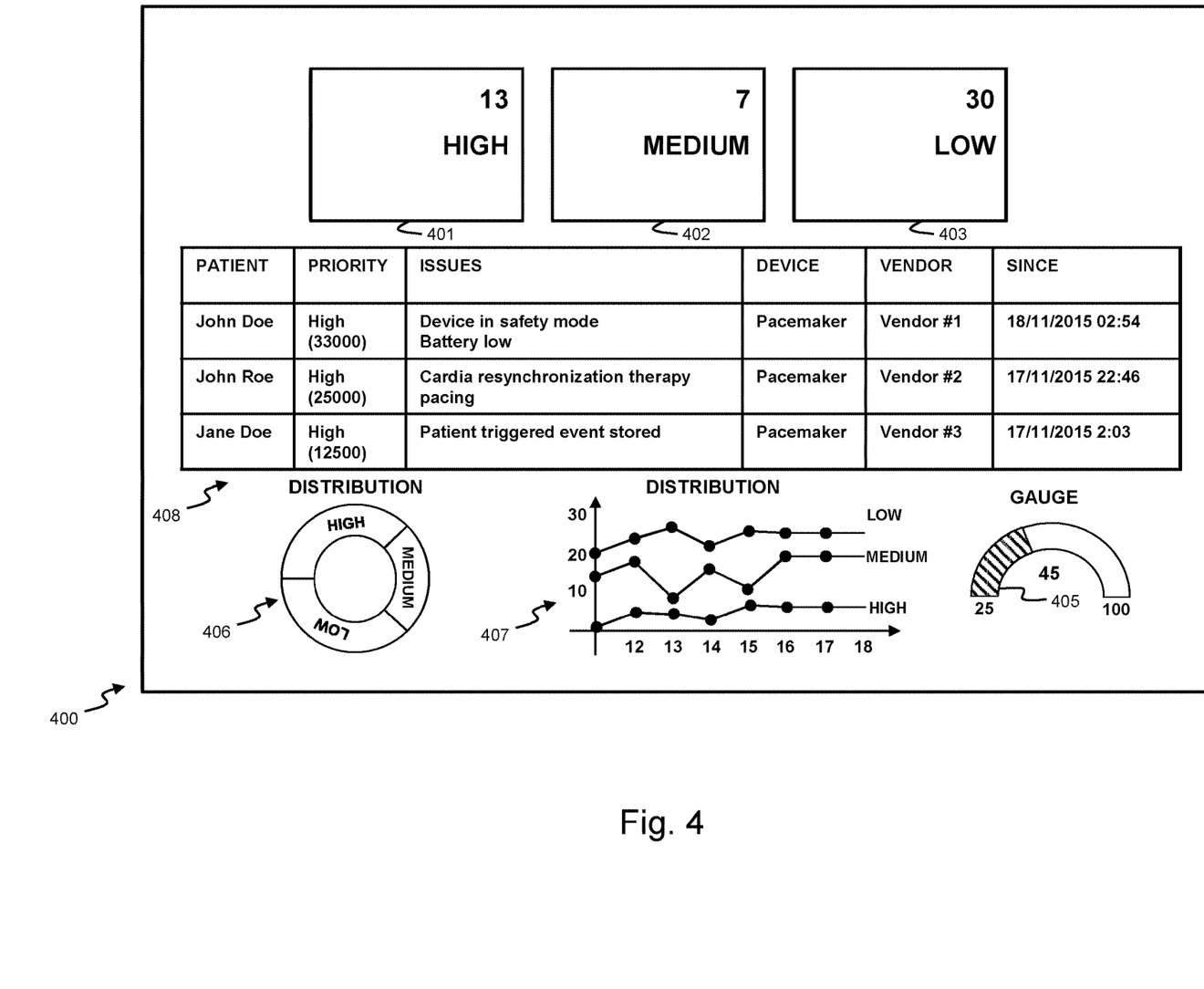
FIG. 4 illustrates a display comprising a classification of patients according to a follow-up priority according to an embodiment of the invention.

FIG. 4 illustrates a screenshot 400 of a user interface presented to user 103 by the system 105 in order to provide medical staff with an overview of all follow-up priorities. The screenshot provides an indication of the priority classes into which the patient are classified under step 215, i.e., 'HIGH', 'MEDIUM' or 'LOW', together with the amount of patients falling under each of the classes. Screenshot 400 further comprises a table 408 providing a listing of the different patients. For each patient the following information is shown: the priority class of the patient together with the follow-up priority; a present issue with the IMD derived from an alert; the type of device, for example a pacemaker; the IMD provider or vendor and the date on which the last alert was received. Preferably the patient are listed from the highest follow-up priority to the lowest.

Screenshot 400 may further show different visualizations 406, 407 of the distribution of the patients in the different priority classes. Screenshot 405 further provides a gauge meter 405 showing an indication of the amount of unhandled alerts relative to a maximum of allowed unhandled alerts.

Figure 5:
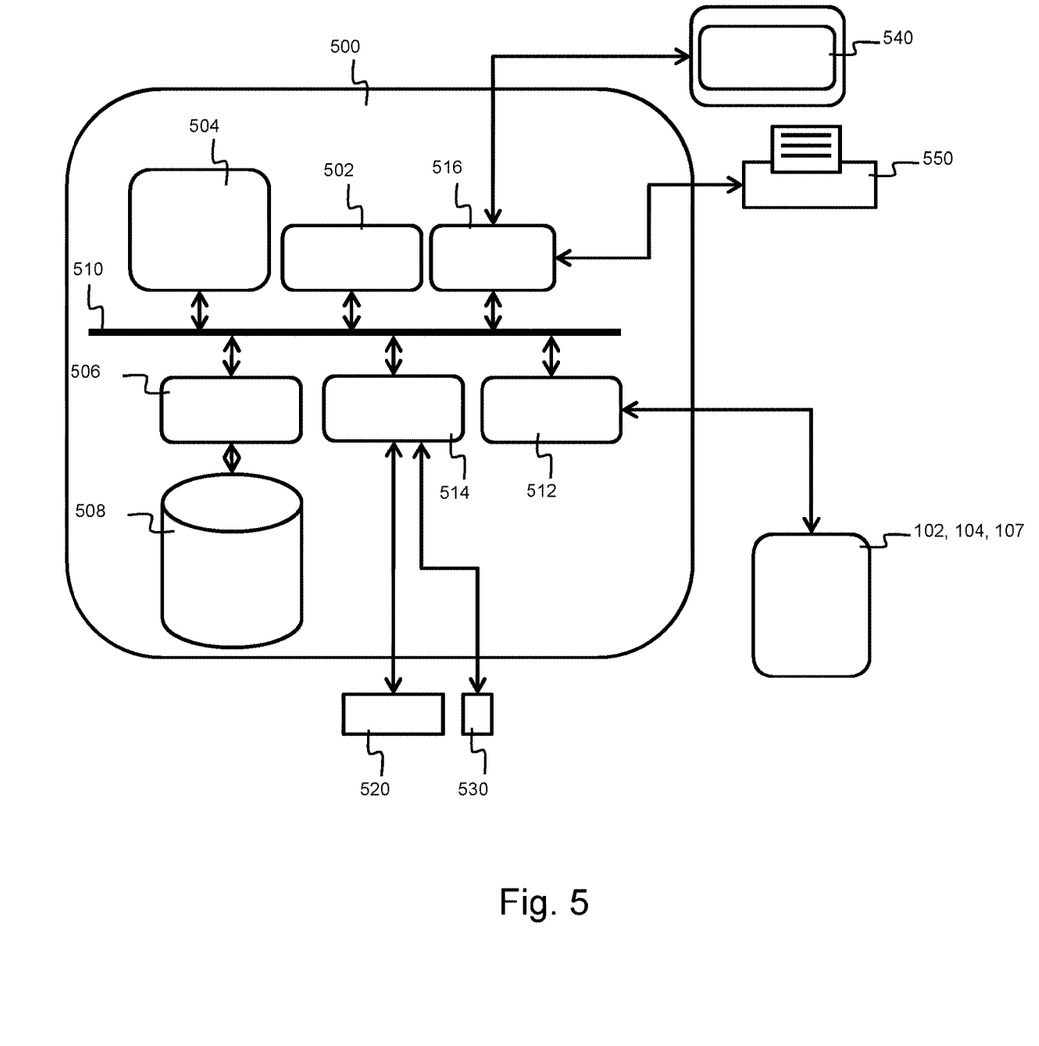
FIG. 5 illustrates a suitable computing system for executing step according to various embodiments of the invention.

FIG. 5 shows a suitable computing system 500 for performing the steps according to the above embodiments. Computing system 500 may be used as computing system 105. Computing system 500 may in general be formed as a suitable general purpose computer and comprise a bus 510, a processor 502, a local memory 504, one or more optional input interfaces 514, one or more optional output interfaces 516, a communication interface 512, a storage element interface 506 and one or more storage elements 508. Bus 510 may comprise one or more conductors that permit communication among the components of the computing system 500. Processor 502 may include any type of conventional processor or microprocessor that interprets and executes programming instructions. Local memory 504 may include a random access memory (RAM) or another type of dynamic storage device that stores information and instructions for execution by processor 502 and/or a read only memory (ROM) or another type of static storage device that stores static information and instructions for use by processor 502. Input interface 514 may comprise one or more conventional mechanisms that permit an operator to input information to the computing device 500, such as a keyboard 520, a mouse 530, a pen, voice recognition and/or biometric mechanisms, etc. Output interface 516 may comprise one or more conventional mechanisms that output information to the operator, such as a display 540, a printer 550, a speaker, etc. Communication interface 512 may comprise any transceiver-like mechanism such as for example one or more Ethernet interfaces that enables computing system 500 to communicate with other devices and/or systems such as IMD provider 102, patient management system 107 or client device 104. The communication interface 512 of computing system 500 may be connected to such another computing system by means of a local area network (LAN) or a wide area network (WAN) such as for example the internet. Storage element interface 506 may comprise a storage interface such as for example a Serial Advanced Technology Attachment (SATA) interface or a Small Computer System Interface (SCSI) for connecting bus 510 to one or more storage elements 508, such as one or more local disks, for example SATA disk drives, and control the reading and writing of data to and/or from these storage elements 508. Although the storage elements 508 above is described as a local disk, in general any other suitable computer-readable media such as a removable magnetic disk, optical storage media such as a CD or DVD, -ROM disk, solid state drives, flash memory cards, . . . could be used. The system 500 described above can also run as a virtual machine above the physical hardware.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A computer-implemented method for handling an Implantable Medical Device, IMD, transmission from an IMD provider; and
    wherein the IMD transmission is related to a patient and comprises one or more alerts and/or IMD data attributes indicative for a status of the IMD or the patient; and
    wherein an alert comprises a provider specific alert priority;
    wherein the method comprises the following steps:
    providing a non-transitory computer-readable medium comprising instructions executable by a computing system of an 1 MB alert-management system for automatically performing the method;
    retrieving the IMD transmission from the 1 MB provider; and
    assigning to the one or more alerts generic alert severity based on a predetermined mapping between the provider specific alert priority and the generic alert severity;
    and/or calculating an IMD data severity based on the IMD data attribute; and
    calculating a transmission severity based on the generic alert severity assigned to the one or more alerts and/or the 1 MB data severity.

2. The method according to claim 1 wherein the method further comprises:
    overriding the generic alert severity of each of the one or more alerts by an alert specific override factor associated with a type of the respective alert or the patient.

3. The method according to claim 1 wherein the calculating the transmission severity comprises calculating a weighted sum between the IMD data severity and the generic alert severity of the one or more alerts of the IMD transmission.

4. The method according to claim 1 wherein the method further comprises calculating a patient follow-up priority based on the transmission severity.

5. The method according to claim 4 wherein the calculating the patient follow-up priority is further based on a patient specific weight factor.

6. The method according to claim 4 wherein the calculating the patient follow-up priority is further based on one or more weighted earlier transmission severities obtained from earlier IMD transmissions.

7. The method according to claim 6 further comprising classifying the patient into a priority group according to the calculated patient follow-up priority.

8. The method according to claim 7 wherein the priority group is selected from the group of:
    a first level indicative for a low medical priority, and
    a second level indicative for a medium medical priority, and
    a third level indicative for a high medical priority.

9. A computer program product comprising computer-executable instructions for performing the method according to claim 1 when the program is run on a computer.

10. A data processing system programmed for carrying out the method according to claim 1.

11. The computer-implemented method of claim 1, wherein the computing system comprises a bus, a processor, a memory, and a storage device.

\* \* \* \* \*